United States Patent
Raju et al.

(10) Patent No.: US 10,099,044 B2
(45) Date of Patent: Oct. 16, 2018

(54) ULTRASOUND MEDIATED DELIVERY WITH CRITICAL-ORGAN PROTECTION

(71) Applicant: KONINKLIJKE PHILIPS N.V., Eindhoven (NL)

(72) Inventors: Balasundar Iyyavu Raju, Chester, NY (US); Christopher Stephen Hall, Kirkland, WA (US); Ralf Seip, Carmel, NY (US); Todd Nicholas Erpelding, University City, MO (US)

(73) Assignee: Koninklijke Philips N.V., Eindhoven (NL)

( * ) Notice: Subject to any disclaimer, the term of this patent is extended or adjusted under 35 U.S.C. 154(b) by 304 days.

(21) Appl. No.: 14/348,122

(22) PCT Filed: Sep. 27, 2012

(86) PCT No.: PCT/IB2012/055146
§ 371 (c)(1),
(2) Date: Mar. 28, 2014

(87) PCT Pub. No.: WO2013/046143
PCT Pub. Date: Apr. 4, 2013

(65) Prior Publication Data
US 2014/0243736 A1  Aug. 28, 2014

Related U.S. Application Data

(60) Provisional application No. 61/540,572, filed on Sep. 29, 2011.

(51) Int. Cl.
*A61M 37/00* (2006.01)

(52) U.S. Cl.
CPC . *A61M 37/0092* (2013.01); *A61M 2037/0007* (2013.01)

(58) Field of Classification Search
CPC ........ A61M 37/0092; A61M 2037/007; A61M 1/3496; A61M 37/0076
USPC ............................ 604/19–24, 500, 506, 290
See application file for complete search history.

(56) References Cited

U.S. PATENT DOCUMENTS

| 6,165,440 A | 12/2000 | Esenaliev |
| 2003/0187371 A1* | 10/2003 | Vortman ................. A61N 7/02 601/3 |
| 2008/0110958 A1 | 5/2008 | McKenna |

(Continued)

FOREIGN PATENT DOCUMENTS

| CN | 101389273 A | 9/2012 |
| EP | 2305216 A1 | 4/2011 |
| WO | 2008110958 A1 | 9/2008 |

*Primary Examiner* — Bradley J Osinski
*Assistant Examiner* — Hamza Darb

(57) ABSTRACT

A device for delivery of a substance (144) using energy to protect, at a site of activation, against a side effect of another substance (156) that was delivered, is being delivered, and/or will be delivered, at another site. The activation may be non-invasive, remote and the energy beam (140) may be an ultrasound beam. A first of the substances can be activated at a particular energy level, and the second is then activated at a lower level so that a population of particles bearing the first substance is not inadvertently activated during activation of the second substance. The device may comprise a system to control the levels of energy applied.

6 Claims, 4 Drawing Sheets

(56) References Cited

U.S. PATENT DOCUMENTS

| | | | |
|---|---|---|---|
| 2010/0106078 A1* | 4/2010 | Dimitrova | A61B 8/481 |
| | | | 604/22 |
| 2010/0209525 A1 | 8/2010 | Bohmer | |
| 2010/0239502 A1* | 9/2010 | Santo | C12N 15/1086 |
| | | | 424/9.6 |
| 2011/0125080 A1 | 5/2011 | Shi | |
| 2011/0263967 A1* | 10/2011 | Bailey | A61B 8/085 |
| | | | 600/411 |
| 2014/0134234 A1 | 5/2014 | Grayburn et al. | |

* cited by examiner

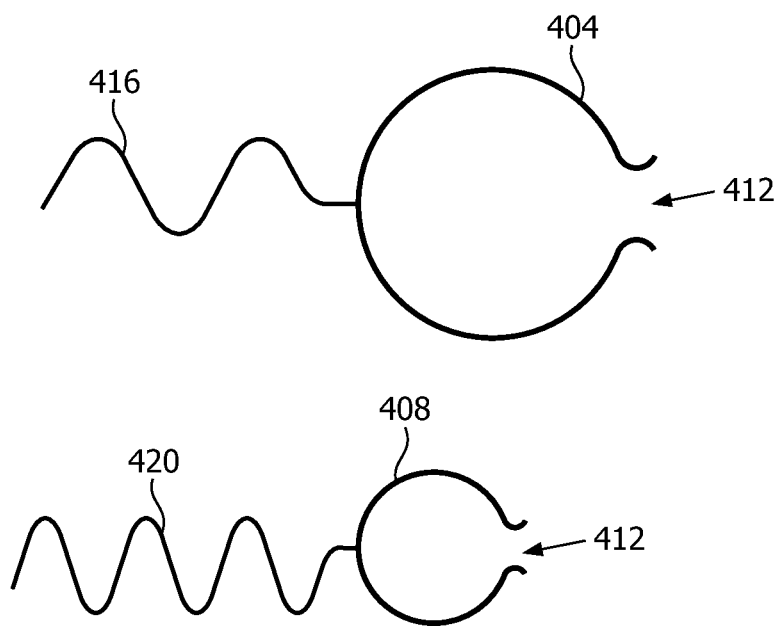
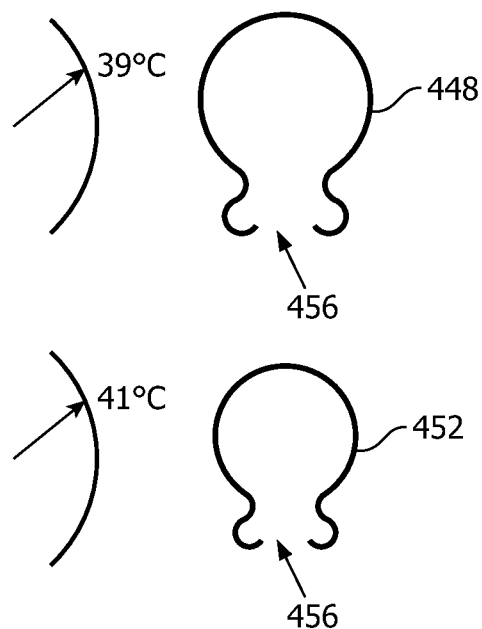
FIG. 4A
FIG. 4B

ULTRASOUND MEDIATED DELIVERY WITH CRITICAL-ORGAN PROTECTION

CROSS-REFERENCE TO PRIOR APPLICATIONS

This application is the U.S. National Phase application under 35 U.S.C. § 371 of International Application No. PCT/IB2012/055146, filed on Sep. 27, 2012, which claims the benefit of U.S. Provisional Patent Application No. 61/540,572, filed on Sep. 29, 2011. These applications are hereby incorporated by reference herein.

FIELD OF THE INVENTION

The present invention relates to activating delivery of a substance and, more particularly, to activating to protect, at a site of the activation, against side effects of another substance delivered at another site.

BACKGROUND OF THE INVENTION

When chemotherapy is used to treat cancer cells measures are taken to limit side effects that otherwise might affect parts of the body not associated with the cancer. Examples of chemotherapeutic agents include the following: alkylating agents such as cisplatin, and carboplatin that chemically modify the cell's DNA which ultimately leads to apoptosis; anthracyclines such as doxorubicin that inhibit DNA and RNA synthesis and prevent replication of the rapidly-growing cancer cells; plant alkaloids such as paclitaxel and docetaxel that work by interfering with the normal microtubule formation during cell division.

The unwanted side effects may be short-term, long term, or permanent, even death. Chemotherapy can cause permanent damage to other organs such as the heart, liver, kidney, lungs, and reproductive organs. For example, cardiotoxicity is a common problem for anthracycline based treatment and is caused by many factors such as free radical formation in the heart or buildup of metabolic products of the anthracycline in the heart. Other side effects from chemotherapy include pain, diarrhea, constipation, mouth sores, hair loss, nausea and vomiting, as well as blood-related side effects.

Chemoprotective agents protect healthy tissue from the toxic effects of cancer drugs. For example, cardioprotective agents such as dexrazoxane can be used to reduce the effect of cardiotoxity. Another example is S-2-3-aminopropil amino ethyl phosphorotioic acid, commonly known as Amifostine™. It was approved by the Federal Drug Administration (FDA) in 1995. It helps to reduce the level of renal injury in cancer patients treated with chemotherapy through myelosuppression of alkylating agents.

Ultrasound mediated delivery of drugs, genetic materials, and other therapeutic agents are promising applications of ultrasound therapy. In these approaches, particles (nanoparticles, liposomes, microcapsules, microbubbles, etc.) incorporate therapeutic agents onto the surface, within the outer coating, within the core of the particle, or in proximity to the particles. Spatially localized treatments are achieved by site-targeted delivery with specific targeting ligands, but also through exposure of a volume of tissue to activating ultrasound energy. Targeting ligands enable binding to specific pathological epitopes and can be incorporated onto the particle surface through avidin-biotin linkages, chemical, or electrostatic interactions. Ultrasound is then introduced to enhance release of the drug. The mechanisms for ultrasound mediated delivery are dependent on the type of particle and ultrasound exposure but can be generally characterized as mechanical (pressure, radiation force, acoustic cavitation) or thermal effects.

Damage to other tissues and organs is an unwanted side effect of many treatment methods such as chemotherapy. All chemotherapeutic methods lead to depression of immune system through decrease in white blood cell, red blood cell, and platelet counts. Liposomal and site targeted formulations have decreased side effects, because delivery of the chemotherapy drug is localized to the site in the body to which ultrasound is applied. However, the side effects, although decreased, are not eliminated. Cardiotoxicity, one of the serious side effects, often presents as EKG changes and arrhythmias, or as a cardiomyopathy leading to congestive heart failure, sometimes presenting many years after treatment. Due to this, there is a maximum cumulative lifetime dose that a patient can be administered. Treatment is usually stopped upon reaching the maximum cumulative dose of the particular anthracycline. The chemotherapy treatment requires careful monitoring of cardiac function with radionuclide angiography. The patient is required to make several visits to the clinic or hospital for treatment.

While the chemoprotective agents can be used to reduce the side effects, the drug and chemoprotective agents cannot be administered simultaneously since they are intended to have opposite effects on the cells.

The cytotoxic effects of doxorubicin exist for several hours, which is helpful to achieve a sufficient level of cell death at the tumor site; however, this causes prolonged exposure to other critical organs as well.

SUMMARY OF THE INVENTION

What is proposed herein is directed to addressing one or more of the above concerns. It would be highly desirable to protect critical organs such as the heart while or immediately after the chemotherapy agent is delivered to the intended cancer site. Thus it is necessary to have a drug delivery method and apparatus that can selectively deliver both components to respective tissues simultaneously or within a short period of time (e.g. minutes). Such a method would enable required doses of chemotherapy drugs to be administered while reducing toxicity to other organs.

Protein- and polymer-shelled microbubbles can be configured to burst, releasing the drug they bear, at specific acoustic intensity, or pressure, thresholds. The thresholds vary with the size and shell thickness of the microbubble and with the material of the shell.

These kinds of microbubbles in particular persist in the circulation for minutes and even longer for some polymer-shelled bubbles.

It would therefore be desirable to selectively deliver locally the drug payload of microbubbles so that it can be taken up locally for protective effect without inadvertently doing the same for microbubbles that have persisted, washed in and bear a drug inducing the opposite effect for the underlying malady. Likewise, it would be desirable to selectively deliver locally the protective agent payload without having those microbubbles that persist be inadvertently activated to delivery when and where the drug for the underlying malady is released to its respective locality.

In an aspect of the present invention, a device includes an energy beam applicator configured for activating, at a site, delivery of a substance for protecting against a side effect of another (or "second") substance at least one of delivered, being delivered, and to be delivered at another (or "second") site. The device is configured for detecting that a current energy-related parameter exceeds a substance-activation-energy-distinguishing threshold and, responsive to the detecting that the threshold is exceeded, intervening.

In a sub-aspect, the threshold is based on an energy-beam level needed to activate delivery of the substance whose delivery is activatable at a higher of the two levels.

In further sub-aspect, the applicator is configured for the activating by issuing energy beams that include ultrasound. The parameter corresponds to a current energy-beam-level setting of the applicator. The threshold provides at least a 0.1 megapascal (MPa) difference between the setting and the above-described energy-beam level needed.

In an alternative sub-aspect, the parameter corresponds to a current energy-beam-level setting of the applicator, and the intervening includes automatically changing the setting and/or requiring that the setting be changed before releasing a hold on system operation.

In an additional sub-aspect, the device is configured for issuing energy beams at respective levels for the activating such that the issuing at the higher level is confined within a time period that precedes administration of the substance whose delivery is activatable at the lower level.

In one further sub-aspect, the second substance includes a therapeutic agent, and a side effect includes a medical side effect in a body in which the deliveries are performed.

The present invention, in a particular aspect, non-invasively activates delivery of a substance to protect, at a site of the activation, against a side effect of another (or "second") substance at least one of delivered, being delivered, and to be delivered, at another (or "second") site.

In an alternative or supplemental sub-aspect, the activating includes remote activation.

In another alternative or supplemental sub-aspect, the activating may include applying an energy beam.

In yet another embodiment, delivery at both sites is subject to activation. Delivery vehicles for the two substances are configured for distinguishing between the activations at the two sites by at least one of a) respective frequencies needed for activation and b) respective accumulated thermal effect needed for activation In a further alternative or supplemental aspect, activating the delivery at the first site includes noninvasively activating a population of first particles located at the first site.

In a sub-aspect of the above, the activating at the second site analogously includes noninvasively activating a population of second particles located at the second site.

As a further sub-aspect, the two populations are configured with respective activation thresholds. The latter are characterized by acoustic pressure correspondingly needed to cause the activating of the two populations and subject to the acoustic pressure applied at a lower to the two threshold being too low to activate the population having a higher of the two thresholds.

As a yet further sub-aspect, the activating of the two populations correspondingly causes release of the first and second substances.

Alternatively or in addition, the first and second substances are injected sequentially in order of highest activation threshold.

In a sub-version of this, the activating of the first and second populations is performed in the above-indicated order, i.e., of highest activation threshold.

As a further sub-version, the activating of the first population is performed after the injecting of the first substance. Analogously, in some embodiments, the activating of the second population is performed after the injecting of the second substance.

In a yet further sub-version, the pressure is applied to at least meet a higher of the two thresholds. The applying is confined within a time period that precedes the injecting of the one of the two substances whose corresponding one of the first and second populations is activated at a lower of the two thresholds.

Details of the novel side-effect protection based on non-invasively delivered substances is set forth further below, with the aid of the following drawings, which are not drawn to scale.

BRIEF DESCRIPTION OF THE DRAWINGS

FIGS. 4A, 4B are conceptual diagrams providing examples of how delivery vehicles can be configured for different release mechanisms.

DETAILED DESCRIPTION OF EMBODIMENTS

Figure 1:
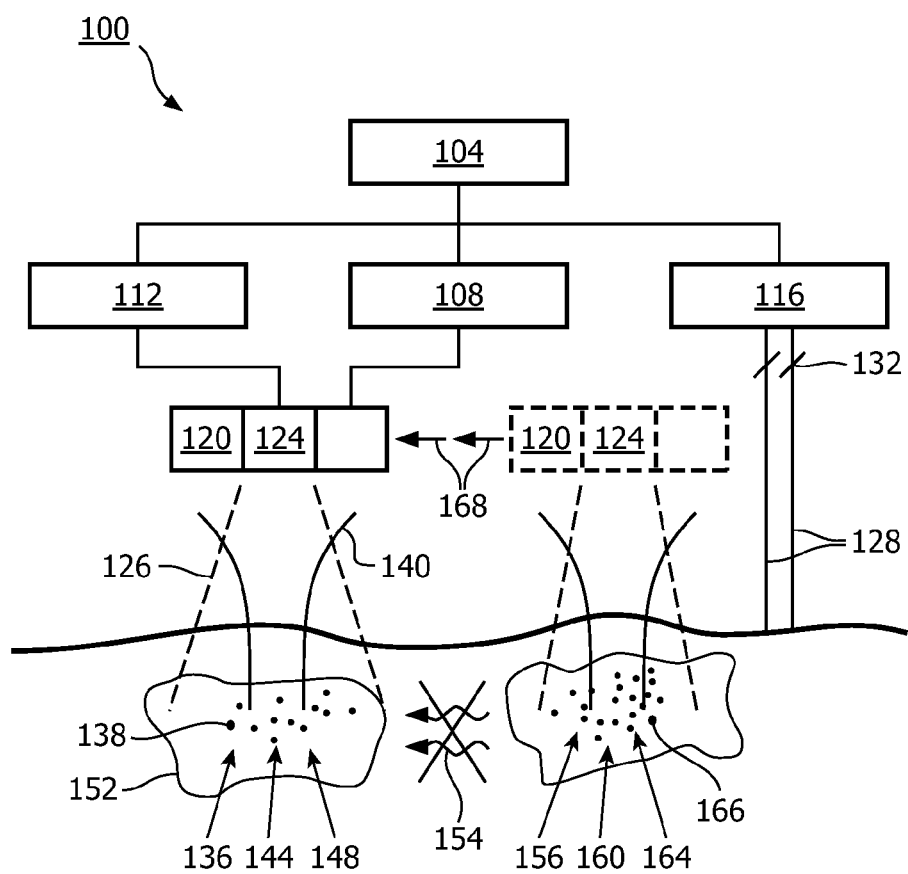
FIG. 1 is a schematic diagram of an exemplary system for non-invasively activating protection against side effects.

FIG. 1 portrays an exemplary system 100 for non-invasively activating protection against side effects. The side effects from which avoidance or for which mitigation is sought could manifest in body organs such as the heart, liver, kidney, lungs, and reproductive organs.

The system 100 includes a controller 104, an energy-beam applicator such as an ultrasound therapy system 108, an ultrasound imaging system 112, and a dispenser such as an injection system 116. The system 100 further includes an ultrasound therapy transducer 120 controlled by the therapy system 108, and an ultrasound imaging transducer 124 controlled by the ultrasound imaging system 112. The two transducers 120, 124 may be arranged confocally, as shown in FIG. 1, or in another arrangement. A treatment region, which may correspond to a focal spot in the case of a focused or weakly focused therapy transducer 120, is within a field of view 126 of the imaging transducer 124. Alternatively, a single transducer can be designed to serve the imaging and therapy functions. The dispenser 116 includes two intravenous (IV) lines 128 and respective, substance storage containers (not shown). One line 128 and container is for the substance used in the underlying therapy. The other line 128 and container is for the substance used for protection from the side effects. The dispenser 116 further has an adjustor 132 for adjusting flow in each line 128. A device, as claimed herein below, may be implemented as the system 100, the controller 104, or one or more integrated circuits embodying an algorithm for activating protection. The algorithm can reside in any kind of read-only memory (ROM) or random access memory (RAM), and may be received by the controller 104 by wire input, or wirelessly via an antenna and from a remote transmitting antenna. In either case, the signal to be transmitted is generated by appropriately varying an electrical current. Other control information, or data, can likewise be embodied within the signal.

A population 136 (hereinafter referred to as a "first population") of particles 138 such as microbubbles is shown in FIG. 1 to be activated by an energy beam 140. Here, the beam 140 is an ultrasound beam, but another type of beam such as a magnetic, electromagnetic or thermal beam could be utilized. The particles 138 of the first population 136, and of a second population discussed below, can be microbubbles, but may be nanoparticles, liposomes, or microcapsules for example.

The insonation activates the first population 136, thereby causing the particles to release their payload substance for local uptake and protection against side effects. Here, the substance is referred to as a "first substance" 144. It is in borne by or otherwise in proximity of the particles of the first population 136. A site 148 of the activation and of where the first population 136 is disposed is referred to as a "first site." The first site 148 may be located within a body organ 152, for instance. The therapy transducer 120 therefore remotely, and noninvasively, activates the first population 136 sufficiently to cause local delivery of the first substance 144.

The first substance 144 is a protective agent administered to avoid or mitigate side effects 154 (shown in FIG. 1 with an "X" through them) of a previously administered second substance 156.

The second substance 156, for treating the underlying malady, was delivered at a second site 160. At the second site 160, a second population 164 of particles 166 bearing or otherwise in proximity of the second substance was disposed and activated for the delivery. At that time, the therapy transducer 120, typically housed in a probe, was directed at the second site 160. The transducer 120 has since been moved (as indicated by the arrows 168), manually for example, to the current, i.e., first, site 148. Alternatively, the movement could have been made mechanically, or "virtually" by means of switching to a different probe with its own respective therapy/imaging transducer.

Although administration of the first and second substances 144, 156 via the respective IV lines 128 may be managed by the controller 104, it may alternatively be performed manually via the line or needle injection.

Figure 2:
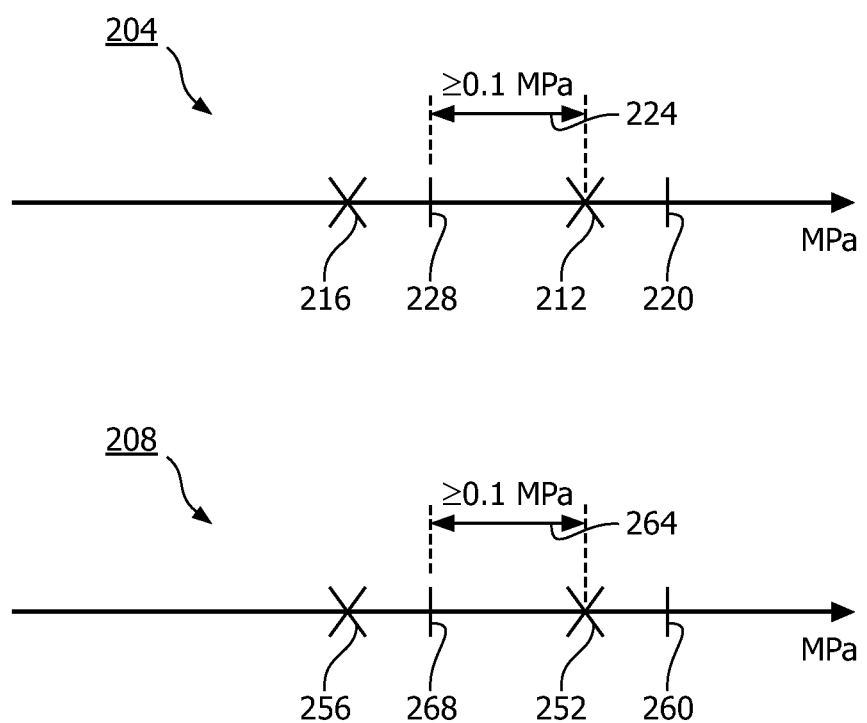
FIG. 2 is a conceptual diagram of two possible embodiments using the system in FIG. 1.

Two possible embodiments 204, 208 for non-invasively activating protection against side effects are shown in FIG. 2.

In the first embodiment 204, delivery of the drug 156 for treating the underlying malady precedes delivery of the protective agent 144. The second population 164 is activatable at a relatively high acoustic pressure 212 (or "high activation threshold"), i.e., the acoustic pressure needed to activate the second population 164 for delivery of the drug 156. The high acoustic pressure 212 is higher than a relatively low acoustic pressure 216 (or "low activation threshold") needed to activate the first population 136 to deliver the protective agent 144. The particles of the first and second populations 136, 164 are configured, in terms of size, shell thickness and shell composition, for delivery-activation at the respective thresholds 216, 212. Methods for forming separate populations of microbubbles that are largely uniform and are therefore configurable for destruction at separate, set acoustic energy levels are disclosed in commonly-assigned US Patent Publication No. 2010/0209525 to Bohmer et al., entitled "Methods for Preparing Polymer Particles," the disclosure of which is incorporated by reference herein in its entirety. The thresholds 212, 216 vary directly with shell thickness, vary inversely with radius and are dependent upon shell composition.

An upper limit 220 on the high activation threshold 212 is constrained by medical considerations of maximum energy exposure.

An actual level of an energy beam, which is here ultrasound, applied to activate the second population 164 to delivery may likewise be limited from above by the upper limit 220 of the high activation threshold 212.

The actual acoustic pressure applied to activate the first population 136 to delivery is, for safety, limited from above by a pre-set pressure difference 224 below the high activation threshold 212. This point which falls below the high activation threshold 212 by the pre-set pressure difference 224 is termed a "substance-activation-energy-distinguishing threshold" 228. The pressure difference 224 is at least 0.1 megapascal (MPa), as denoted in FIG. 2. Sample ranges for the acoustic pressure applied to meet the low and high activation thresholds 216, 212, respectively, are 0.3 to 0.4 MPa and 0.6 to 0.8 MPa, with a pressure difference 236 of between 0.3 and 0.4 MPa.

In effect, the system 100 may be configured, as a matter of safety, to restrict, for the two deliveries, respective levels of energy beams issued, such that a lower of the two levels is insufficient to activate delivery of the substance whose delivery is activatable at a higher of the two levels.

In the present embodiment, this means that the acoustic pressure from the ultrasound therapy transducer 120 is prevented, while the protective agent 144 is delivered, from reaching the high activation threshold 212. Otherwise, that activation of the protective agent 144 might inadvertently activate any of the drug 156 now present at the "protective" activation site 148 that was administered for the underlying malady, and thereby mitigate the protective effect.

What is more, to provide a safety margin and as mentioned herein above, the acoustic pressure may be prevented, while the protective agent 144 is delivered, from coming within a particular range, i.e., whose length is the pressure difference 224, of the high activation threshold 212.

The device 110 will intervene upon detecting that a current energy-related parameter such as the current energy-beam-level setting exceeds the substance-activation-energy-distinguishing threshold 228. The intervention may entail automatically changing, i.e., lowering, the setting or requiring that the setting be changed before releasing a hold on system operation.

The second embodiment 208 differs from the first embodiment 204 in that delivery of the drug 156 for treating the underlying malady occurs after, rather than before, delivery of the protective agent 144. This could be represented in FIG. 1 as a reversal in the direction of the arrows 168. Consequently, it is the first population 136 bearing or otherwise in proximity of the protective agent 144, in the second embodiment, that has a high activation threshold 252; conversely, it is the second population 164 which bears or otherwise is in proximity of the underlying-malady-treating drug 156 and which has a low activation threshold 256. The high activation threshold 252 is bounded by an upper limit 260. The low activation threshold 256 is, by at least a pressure difference 264, less than a substance-activation-energy-distinguishing threshold 268. For reasons analogous to those discussed above with regard to the first embodiment 204, the pressure difference 264 is, likewise for the second embodiment 208, at least 0.1 megapascal (MPa). Also, the acoustic pressure may be prevented, while the drug 156 for the underlying malady is delivered, from coming within a particular range, i.e., whose length is the pressure difference 264, of the high activation threshold 252. The intervention above-noted for the first embodiment operates analogously for the second embodiment.

Figure 3:
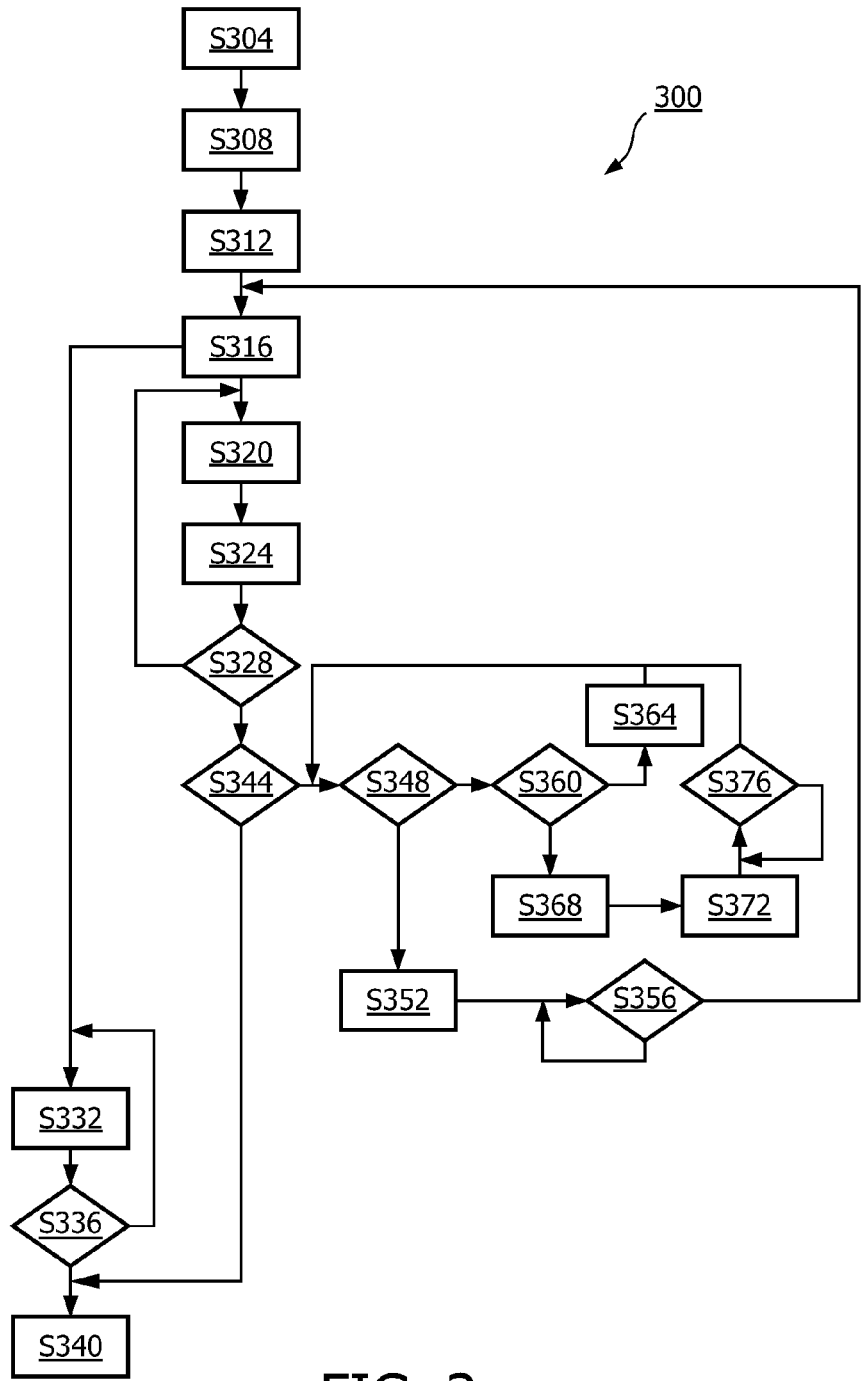
FIG. 3 is a flow chart providing more details of how operation according to FIG. 2, using the system of FIG. 1, could proceed.

FIG. 3 details, by way of illustrative and non-limitative example, a procedure 300 for non-invasively activating protection against side effects. Operationally, the type of particles 138, 166 that will make up the first and second populations 136, 164 are each configured with appropriate dimensional and compositional parameters so that the respective activation thresholds 212, 216 can accommodate the required pressure difference 224, 264 (step S304). The system 100 is initialized with the substance-activation-energy-distinguishing threshold 228, 268, which is the high activation threshold 212, 252 less the respective pressure difference 224, 264 (step S308). The substance 156, 144 with the high activation threshold 212, 252 is selected (step S312). This corresponds to a selection that may have inherently been made between the two embodiments 204, 208 in the previous step S304, to the extent population parameters were tailored to the respective substance 156, 144. Injection now begins of the selected substance 156, 144, including the particles 138, 166 that bear or are otherwise in vicinity of the substance (step S316). Under real-time image guidance provided by the imaging system 112, activating of delivery at the current site 148, 160 at which the imaging and therapy are directed proceeds, automatically and without need for user intervention (step S320). In particular, monitoring commences for when blood flow in the vasculature washes into the current site 148, 160 the population 136, 164 to be activated for delivery. Exemplary monitoring/activation techniques are described in more detail in the commonly-assigned patent application entitled "Automated Ultrasound Mediated Delivery." The activation for delivery releases the current substance 144, 156 for local delivery (step S324). The dose of the current substance 144, 156 may at this point be incomplete. Firstly, the total amount of the current substance 144, 156 released locally for uptake by the local body tissue may not be available in sufficient quantity in a single instance of activation, i.e., pulse or pulse series. Thus, a number of iterations may be needed at the current site 148, 160, with a wait in between iterations for replenishment of the particles 138, 166 destroyed by the activating energy. Secondly, the body organ 152 currently undergoing therapy, underlying or protective, may, in the case of a focused, or weakly focused, beam not totally be covered by the focal spot. In this event, the beam is redirected, electronically, mechanically or manually, to a next spot, and so on.

If the dose for the current substance 144, 156 is incomplete (step S328), processing branches back to step S320, possibly with energy-beam focal-point translation as appropriate, if and when needed. An automated treatment plan may be continually estimating accumulated dosage, and keeping track of treatment locations if there is more than one as in the case of focused or weakly focused ultrasound.

Meanwhile, when injection was commenced in step S316, a continual adjustment process began of the inflow of the current substance 144, 156, and the particles 138, 166 which bear or are otherwise in proximity of the substance (step S332). In particular and by way of example, the dispenser 116 is operated in real time under image guidance to adjust the rate of flow of the current substance 144, 156 and associated particles 136, 164 in the respective IV line 128 so that the particles come within an imaging field of view 126 within an expected time period. The inflow can alternatively be adjusted manually.

When the dose for the current substance is, according to the step 328, complete (step S336), the inflow is halted (step S340).

Query is now made as to whether one of the two substances 144, 156 has not yet been administered (step S344). In the case of an automated treatment plan, the system 100 is aware of when the treatment for the current site 148, 160 is complete, and that more treatment remains to be performed. Other indicators that the treatment is now transitioning to the, as yet, untreated site 148, 160 include the halting of the inflow in step S340 and possibly sufficient lateral motion of the probe detected by means of an internal motion sensor.

If both substances 144, 156 have been administered (step S344), the procedure 300 has been completed and processing branches to step S340.

Otherwise, if one of the two substances 144, 156 has not yet been administered (step S344), query is made as to whether the current energy-related parameter such as an energy-beam-level setting of the therapy transducer 120 exceeds the respective, pre-stored, substance-activation-energy-distinguishing threshold 228, 268 (step S348).

If the respective threshold 228, 268 is not exceeded (step S348), selection of the current substance 144, 156 is now switched to the one of lower activation threshold 216, 256 (step S352). When a therapy focal point is set for the therapy transducer 120 (step S356), processing returns to step S316. The therapy focal point would be set, e.g., manually by the clinician, at this time for use at the site 148, 160 for delivery of the currently selected substance 144, 156.

Otherwise, if the respective threshold 228, 268 is exceeded (step S348), intervention by the system 100 may occur, for safety reasons. If the intervention is not by means of a hold being placed on system operation (step S360), the intervention occurs by the system 100 automatically lowering the acoustic pressure setting (step S364), and processing then returns to step S348. If, on the other hand, intervention is by means of a hold (step S360), an indication, audible or visible, for example, is made to the clinician, such as an error message (step S368). The system 100 is placed on hold (step S372). When the clinician changes the setting (step S376), processing returns to step S348.

Optionally and alternatively as a third embodiment, both agents can be injected simultaneously. The agent of lower activation threshold, i.e., borne by the particles whose population is activated at the lower threshold, is activated first. This occurs at the site in need of treatment, to treat the underlying malady. However, the treatment continues until all of the particles bearing this agent are used up. At that point, all that remain are the particles of higher activation threshold. The point of therapy is moved to the respective site where protection is sought. The acoustic pressure is then increased to activate the remaining particles. Alternatively, the agent of lower threshold can be the protective agent, rather than the therapeutic agent. Conversely, in that case, the agent of higher threshold would be therapeutic agent.

More generally therefore, what is proposed herein relates to activating delivery, at a site, of a substance for protecting against a side effect of another substance delivered (as in the first embodiment), being delivered (as with simultaneous activations at respective sites in the third embodiment), and/or to be delivered (as in the second embodiment) at another site. The third embodiment can be executed so that, at the time protection is activated, the therapeutic substance is any combination of delivered, being delivered and to be delivered.

FIGS. 4A, 4B portray respective release mechanisms other than acoustic pressure.

In FIG. 4A, delivery vehicles 404, 408 for the two substances are configured for distinguishing between the activations at the two sites. In particular, the delivery vehicles i.e., particles such as microbubbles, of one population are designed relatively large. These tend to burst 412 with a ultrasound of relatively low excitation frequency 416. Conversely, microbubbles of the other population are designed relatively small and therefore tend to burst 412 with ultrasound of relatively high excitation frequency 420.

The two frequencies 416, 420 might be, for example, 0.5 MHz apart. These two populations can serially injected as in the previous embodiments, or co-injected because activation at one frequency 416, 420 will not, to any significant degree, activate the other population. Activation of the two populations can accordingly be performed in either order, or simultaneously. An advantage of simultaneous activation is that, while the protective effect is realized immediately (as when the protective agent precedes the therapeutic agent), a relatively small dose of the protective agent is required to protect against a given therapeutic dose.

A delivery mechanism in FIG. 4B is thermal based. One agent is encapsulated in a thermally sensitive liposome 448 that has a release temperature of, for example, 39° C., and the second agent is encapsulated in a liposome 452 with a release temperature of 41° C. The applied ultrasound heats and melts the liposome 448, 452, thereby releasing 456 the agent. The protocol here is analogous to each of the first three embodiments utilizing acoustic pressure as the release mechanism, except that here the release mechanism is based on accumulated thermal effect. Thus, a device for performing the method might use, as the current energy-related parameter, the current duration of therapy beam application as an indicator of temperature at the site. The intervention would involve the immediate cutoff of therapy beam application.

Exemplary monitoring techniques for the delivery mechanisms in FIGS. 4A, 4B are disclosed in the commonly-assigned patent application entitled "Assays for Ultrasound Mediated Delivery."

Delivery is activated for a substance to protect, at a site of the activation, against a side effect of another substance that was delivered, is being delivered, and/or will be delivered, at another site. The activation may be non-invasive, remote and by application of an energy beam such as an ultrasound beam. A first of the substances can be activated at a particular energy level, and the second is then activated at a lower level so that a population of particles bearing the first substance is not inadvertently activated during activation of the second substance. An energy beam applicator may be configured for issuing the beams and can be part of a device configured for detecting that a current energy-beam-level setting exceeds a substance-activation-energy-distinguishing threshold and, responsive to the detecting that the threshold is exceeded, intervening regarding changing the setting. The threshold may be based on an energy-beam level needed to activate delivery of the substance whose delivery is activatable at a higher of the two levels.

Applications include chemotherapy and any other treatment method where side effects are to be minimized through protective agents.

While the invention has been illustrated and described in detail in the drawings and foregoing description, such illustration and description are to be considered illustrative or exemplary and not restrictive; the invention is not limited to the disclosed embodiments.

For example, intervention could include vibration of the probe, optionally accompanied with the auditory and/or visual feedback.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A device for ultrasound mediated delivery, the device comprising:
   an energy beam applicator configured for activating delivery of a first substance at a first site and activating delivery of a second substance at a second site, wherein the first substance is a protective agent designed for protecting the first site against an undesirable side effect of a second substance; and
   a controller configured to:
      cause the energy beam applicator to issue an energy beam at the first site and an energy beam at the second site;
      detect an energy level of the energy beam at the first site and an energy level of the energy beam at the second site;
      detect whether the energy level of the energy beam at the first site exceeds a substance-activation-energy-distinguishing threshold that is a preset amount higher than a level of energy necessary to activate the first substance and a preset amount lower than a level of energy necessary to activate the second substance; and
      change the energy level of the energy beam at the first site if the detected level of the energy beam exceeds the substance-activation-energy-distinguishing threshold.

2. The device of claim 1, wherein said applicator is configured for said activating by issuing energy beams that comprise ultrasound, and wherein the pre-set amount is at least a 0.1 megapascal (MPa).

3. The device of claim 1, wherein said changing comprises at least one of automatically lowering the energy level of the energy beam and requiring that a setting be lowered before releasing a hold on system operation.

4. The device of claim 1, wherein said second substance comprises a therapeutic agent, and wherein said side effect comprises an undesirable side effect in an object in which deliveries of the first substance and the second substance are performed.

5. A non-transitory computer readable medium embodied with instructions executable by a processor for carrying out a series of acts, the series of acts comprising:
   transmitting, by a beam applicator, an energy beam at a first site and an energy beam at a second site, wherein the energy beam at the first site activates a first substance and the energy beam at the second site activates a second substance, the first substance comprised of a protective agent designed for protecting the first site against a side effect of the second substance;
   detecting, by a controller operatively associated with the beam applicator, an energy level of the energy beam at the first site and an energy level of the energy beam at the second site;

detecting, by the controller operatively associated with the beam applicator, whether the energy level of the energy beam at the first site exceeds a substance-activation-energy-distinguishing threshold that is a preset amount higher than a level of energy necessary to activate the first substance and a preset amount lower than a level of energy necessary to activate the second substance; and changing, by the controller, the energy level of the energy beam at the first site if the detected level of the energy beam exceeds the substance-activation-energy-distinguishing threshold.

6. The non-transitory computer readable medium of claim 5, wherein the instructions for changing the energy level of the energy beam at the first site include instructions for lowering the energy level of the energy beam or requiring that the energy level of the energy beam be lowered before releasing a hold on system operation.

* * * * *